(12) United States Patent
Ikeda

(10) Patent No.: US 8,921,268 B2
(45) Date of Patent: Dec. 30, 2014

(54) HERBICIDAL COMPOSITION

(71) Applicant: Sumitomo Chemical Company, Limited, Tokyo (JP)

(72) Inventor: Hajime Ikeda, Kasai (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 6 days.

(21) Appl. No.: 13/784,167

(22) Filed: Mar. 4, 2013

(65) Prior Publication Data

US 2013/0237417 A1 Sep. 12, 2013

(30) Foreign Application Priority Data

Mar. 7, 2012 (JP) ................. 2012-050069

(51) Int. Cl.
- *A01N 25/32* (2006.01)
- *A01N 43/80* (2006.01)
- *A01N 43/84* (2006.01)
- *A01N 43/653* (2006.01)
- *A01N 43/54* (2006.01)
- *A01N 33/22* (2006.01)
- *A01N 41/06* (2006.01)

(52) U.S. Cl.
CPC ............. *A01N 43/80* (2013.01); *A01N 43/84* (2013.01); *A01N 43/653* (2013.01); *A01N 43/54* (2013.01); *A01N 33/22* (2013.01); *A01N 25/32* (2013.01); *A01N 41/06* (2013.01)
USPC ........................... 504/112; 504/130; 504/138

(58) Field of Classification Search
USPC .................. 504/112, 118, 130, 138
See application file for complete search history.

(56) References Cited

U.S. PATENT DOCUMENTS

| | | | |
|---|---|---|---|
| 3,928,416 A * | 12/1975 | Bayer et al. | ...... 560/21 |
| 2002/0004457 A1 | 1/2002 | Nevill et al. | |
| 2003/0130120 A1 * | 7/2003 | Ziemer et al. | ...... 504/105 |
| 2007/0010399 A1 | 1/2007 | Rosinger et al. | |
| 2007/0015662 A1 | 1/2007 | Rosinger et al. | |
| 2008/0254985 A1 * | 10/2008 | Zagar et al. | ...... 504/136 |
| 2011/0190131 A1 | 8/2011 | Ikeda | |

FOREIGN PATENT DOCUMENTS

DE 19834627 A1 12/1998

OTHER PUBLICATIONS

HCAPLUS abstract 1981:456203 (1981).*
Watteyne et al., "Isoxaflutole + Cyprosulfamide, Thiencarbazone + Isoxaflutole + Cyrosulfamide: Performance in University Corn Trials," North Central Weed Science Society Proceedings, vol. 64, No. 119, 2009.

* cited by examiner

*Primary Examiner* — John Pak
(74) *Attorney, Agent, or Firm* — Birch, Stewart, Kolasch & Birch, LLP

(57) ABSTRACT

Provided are technologies for controlling weeds, specifically, a herbicidal composition including as active ingredients isoxaflutole, cyprosulfamide, and one or more compounds selected from Group A has weed control effects, Group A:

a group consisting of flumioxazin, sulfentrazone, saflufenacil, oxyfluorfen, fomesafen, and a compound represented by formula (I)

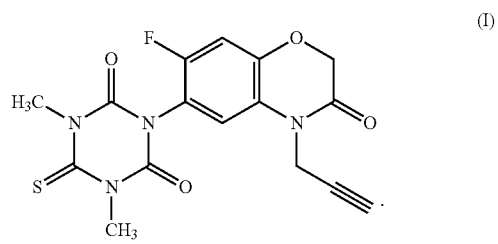

11 Claims, No Drawings

HERBICIDAL COMPOSITION

BACKGROUND OF THE INVENTION

1. Field of the Invention

The present invention relates to a method for controlling weeds.

2. Description of the Related Art

For controlling weeds, many compounds are known as active ingredients of pesticides such as herbicides.

NON-PATENT DOCUMENT

Crop Protection Handbook, vol. 97 (2011) Meister Publishing Company, ISBN:1-892829-23-1)

SUMMARY OF THE INVENTION

The problem to be solved by the present invention is to provide a herbicidal composition capable of exhibiting high controlling activities to weeds.

The present inventor has accomplished the present invention by finding out that a combination of certain specific herbicides can exhibit high controlling activities.

The present invention includes the following:

[1] A herbicidal composition comprising as active ingredients isoxaflutole, cyprosulfamide, and one or more compounds selected from Group A, Group A:
a group consisting of flumioxazin, sulfentrazone, saflufenacil, oxyfluorfen, fomesafen, and compounds represented by formula (I):

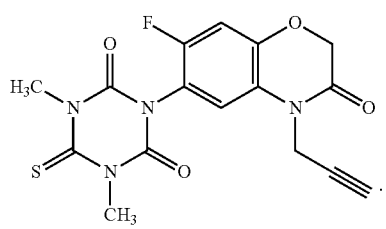

[2] The herbicidal composition according to [1], wherein the weight ratio of the one or more compounds selected from Group A to isoxaflutole is from 1:0.01 to 1:100.

[3] The herbicidal composition according to [1], wherein the weight ratio of the one or more compounds selected from Group A to cyprosulfamide is from 1:0.01 to 1:100.

[4] The herbicidal composition according to any one of [1] to [3], wherein the one or more compounds selected from Group A is flumioxazin.

[5] A weed control method comprising applying isoxaflutole, cyprosulfamide, and one or more compounds selected from Group A simultaneously or in combination to a soil of a place where weeds grow or are to grow, or to weeds, Group A:
a group consisting of flumioxazin, sulfentrazone, saflufenacil, oxyfluorfen, fomesafen, and compounds represented by formula (I):

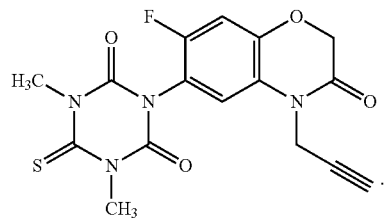

[6] The method according to [5], wherein the weight ratio of the one or more compounds selected from Group A to isoxaflutole is within the range of from 1:0.01 to 1:100.

[7] The method according to [5], wherein the weight ratio of the one or more compounds selected from Group A to cyprosulfamide is within the range of from 1:0.01 to 1:100.

[8] The method according to any one of [5] to [7], wherein the one or more compounds selected from Group A is flumioxazin.

[9] The method according to any one of [5] to [8], wherein the place where weeds grow or are to grow is a soybean field, a cotton field, or a corn field.

[10] The method according to any one of [5] to [8], wherein the place where weeds grow or are to grow is a tree land.

[11] The weed control method according to [9], wherein the soybean of the soybean field, the cotton of the cotton field, or the corn of the corn field is transgenic soybean, transgenic cotton, or transgenic corn.

[12] The weed control method according to [9], wherein the soybean of the soybean field, the cotton of the cotton field, or the corn of the corn field is transgenic soybean, transgenic cotton, or transgenic corn to each of which resistance to herbicides has been imparted.

[13] The weed control method according to [9], wherein the soybean of the soybean field or the cotton of the cotton field is transgenic soybean imparted with resistance to 4-hydroxyphenylpyruvate dioxygenase inhibitors or transgenic cotton imparted with resistance to 4-hydroxyphenylpyruvate dioxygenase inhibitors.

The present invention makes it possible to control weeds in crop fields, vegetable fields, tree lands, or non-cultivated lands with high potency.

DETAILED DESCRIPTION OF THE PREFERRED EMBODIMENTS

The herbicidal composition of the present invention (hereinafter described as present invention composition) comprises a herbicidal composition comprising as active ingredients isoxaflutole, cyprosulfamide and one or more compounds selected from Group A, Group A:
a group consisting of flumioxazin, sulfentrazone, saflufenacil, oxyfluorfen, fomesafen, and compounds represented by formula (I) (hereinafter described as Compound 1):

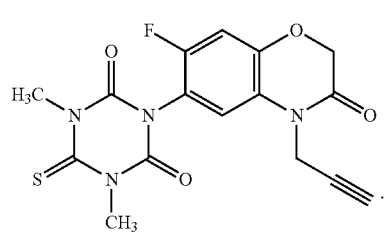

Flumioxazin, sulfentrazone, saflufenacil, oxyfluorfen, fomesafen, and the compounds represented by formula (I) listed in Group A are known as PPO inhibitors.

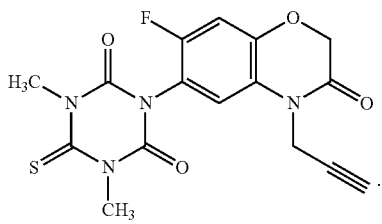
(I)

Flumioxazin, sulfentrazone, saflufenacil, oxyfluorfen, and fomesafen are herbicidally active compounds described in Crop Protection Handbook, Vol. 97 (2011) (Meister Publishing Company, ISBN:1-892829-23-1) and can be produced by a known production method. Moreover, commercially available formulations containing this compound can be got.

Fomesafen to be used for the present invention may be in a salt form like fomesafen-sodium.

The compound of formula (I) is a compound disclosed in WO 02/066471 and can be produced by a known production method.

Isoxaflutole, which is used as an active ingredient of the present invention composition, is a herbicidally active compound described in Crop Protection Handbook, Vol. 97 (2011) and can be produced by a known production method. Moreover, commercially available formulations containing this compound can be got.

Cyprosulfamide, which is used as an active ingredient of the present invention composition, is a compound disclosed in U.S. Pat. No. 6,251,827 and U.S. Pat. No. 7,608,736 and can be produced by a known production method.

The composition of the present invention has herbicidal activity against a wide variety of weeds, and thus enabling effective control of a wide variety of weeds in the fields where crops are usually cultivated with or without tillage, vegetable field, tree land or non-cultivated land. Furthermore, the composition does not cause significant phytotoxicity to useful plants.

Examples of the farm crop field in the present invention include fields of edible crops such as peanut, soybean, corn, wheat and barley; feed crops such as sorghum and oat; industrial crops such as cotton; and sugar crops such as sugarcane. Examples of the vegetable field in the present invention include fields of Solanaceae vegetables such as eggplant, tomato, green pepper, red pepper and potato; Cucurbitaceae vegetables such as cucumber, pumpkin, zucchini, watermelon and melon; Brassicaceae vegetables such as radish, turnip, horseradish, cohlrabi, Chinese cabbage, cabbage, leaf mustard, broccoli and cauliflower; Compositae vegetables such as burdock, crown daisy, artichoke and lettuce; Liliaceae vegetables such as leek, onion, garlic and asparagus; Umbelliferae vegetables such as carrot, parsley, celery and parsnip; Chenopodiaceae vegetables such as spinach and Swiss chard; Lamiacea vegetables such as perilla, mint, basil and lavender; strawberry; sweet potato; yam; and taro.

Examples of the tree land in the present invention include orchards, tea plantation, mulberry field, coffee plantation, banana plantation, palm plantation, flower tree land, flower field, nursery tree land, young plant land, forest and garden. Examples of the orchard include pome fruits such as apple, pear, Japanese pear, Chinese quince and quince; stone fruits such as peach, plum, nectarine, Japanese apricot, cherry, apricot and prune; citrus such as Satsuma orange, orange, lemon, lime and grapefruit; tree nuts such as chestnut, walnut, hazelnut, almond nut, pistachio nut, cashew nut and macadamia nut; berries such as blueberry, cranberry, blackberry and raspberry; grape; persimmon; olive; and loquat.

Examples of the non-cultivated land in the present invention include playground, vacant land, neighborhood of railroad, park, car park, neighborhood of road, dry riverbed, land under power-transmission lines, land for housing and site for factor.

Crops cultivated in the farm crop field in the present invention are not limited as long as they belong to cultivars which are generally cultivated as crops.

These plant cultivars include plants, to which resistance to herbicides has been imparted by a classical breeding method or genetic recombination technology, the herbicides being protoporphyrinogen oxidase inhibitors such as flumioxazin; 4-hydroxyphenylpyruvate dioxygenase inhibitors such as isoxaflutole; acetolactate synthase inhibitors such as imazethapyr and thifensulfuron-methyl; acetyl CoA carboxylase inhibitors such as sethoxydim; 5-enolpyruvylshikimate-3-phosphate synthase inhibitors such as glyphosate; glutamine synthase inhibitors such as glufosinate; auxin type herbicides such as 2,4-D and dicamba; and bromoxynil.

Examples of the crop, to which resistance to herbicides has been imparted by a classical breeding method, include corn which is resistant to an imidazolinone type acetolactate synthase inhibiting herbicide such as imazethapyr, and which has already been sold under the trade name of Clearfield (registered trademark). Such a crop also includes STS soybean which is resistant to a sulfonylurea type acetolactate synthase inhibiting herbicide such as thifensulfuron-methyl. Similarly, examples of the plant, to which resistance to an acetyl CoA carboxylase inhibitor such as a trione oxime or aryloxyphenoxypropionic acid type herbicide has been imparted by a classical breeding method, include SR corn.

Examples of the plant, to which resistance to herbicides has been imparted by genetic recombination technology, include corn, soybean and cotton, each having resistance to glyphosate, and which have already been sold under the trade names of RoundupReady (registered trademark), Agrisure (registered trademark) GT, and Gly-Tol (registered trademark). Similarly, plants, to which resistance to herbicides has been imparted by genetic recombination technology, include corn, soybean and cotton, each having resistance to glufosinate, and they have already been sold under the trade name of LibertyLink (registered trademark). There are corn and soybean cultivars, which are resistant to both glyphosate and ALS inhibitors, and are sold under the trade name of Optimum (registered trademark) GAT (registered trademark). Similarly, there is soybean, to which resistance to an imidazolinone type acetolactate synthase inhibitor has been imparted by genetic recombination technology, and which has been developed under the trade name of Cultivance. Similarly, there is cotton, to which resistance to bromoxynil has been imparted by genetic recombination technology, and which has already been sold under the trade name of BXN (registered trademark).

Crops such as soybean having resistance to dicamba can be fabricated by introducing a dicamba-degrading enzyme such as dicamba monooxygenase isolated from *Pseudomonas maltophilia* into the plant (Behrens et al. 2007 Science 316: 1185-1188).

Crops having resistance to both phenoxy acid type herbicidez such as 2,4-D, MCPA, dichlorprop and mecoprop, and aryloxyphenoxypropionic acid type herbicides such as quizalofop, haloxyfop, fluazifop, diclofop, fenoxaprop, metamifop, cyhalofop and clodinafop can be fabricated by introducing a gene encoding an aryloxyalkanoate dioxygenase (Wright et al. 2010: Proceedings of National Academy of Science. 107(47): 20240-20245).

By introducing a gene encoding a 4-hydroxyphenylpyruvate dioxygenase (hereinafter referred to as HPPD) inhibitor which exhibits resistance to HPPD inhibitor, and thus plants having resistance to the HPPD inhibitor can be fabricated (US2004/0058427). By introducing a gene capable of synthesizing homogentisic acid as a product of HPPD through another metabolic pathway, homogentisic acid is produced even in the presence of a HPPD inhibitor, and thus making it possible to fabricate plants which exhibits resistance to the HPPD inhibitor (WO 02/036787). By introducing a gene capable of excessively expressing HPPD, HPPD is produced in the amount which does not exert an adverse influence on the growth of the plant even in the presence of a HPPD inhibitor, and thus making it possible to fabricate plants which exhibit resistance to the HPPD inhibitor (WO 96/38567). By introducing aforementioned gene capable of excessively expressing HPPD and also introducing a gene encoding a prephenate dehydrogenase so as to increase the production amount of p-hydroxyphenylpyruvic acid as a substrate of HPPD, and thus making it possible to fabricate plants which exhibit resistance to the HPPD inhibitor (Rippert P et al. 2004 Engineering plant shikimate pathway for production of tocotrienol and improving herbicide resistance. Plant Physiol. 134: 92-100).

Examples of the other method of imparting resistance to a herbicide include methods of introducing genes described in WO 98/20144, WO 2002/46387 and US2005/0246800.

Aforementioned crops also include crops which made it possible to synthesize selective toxins known as the genus *Bacillus*, using genetic recombination technology.

Examples of toxins expressed in these transgenic plants include insecticidal proteins derived from *Bacillus cereus* and *Bacillus popilliae*; δ-endotoxins derived from *Bacillus thuringiensis*, e.g. Cry1Ab, Cry1Ac, Cry1F, Cry1Fa2, Cry2Ab, Cry3A, Cry3Bb1, Cry9C, Cry34ab and Cry35ab, and insecticidal proteins such as VIP1, VIP2, VIP3 and VIP3A; insecticidal toxins derived from nematodes; insecticidal toxins produced by animals, such as scorpion toxin, spider toxin, bee toxin and insect-specific neurotoxins; filamentous fungi toxins; plant lectins; agglutinin; protease inhibitor such as trypsin inhibitor, serine protease inhibitor, patatin, cystatin and papain inhibitor; ribosome-inactivating proteins (RIP) such as ricin, corn-RIP, abrin, rufin, sapolin and priodin; steroid metabolic enzymes such as 3-hydroxysteroid oxidase, ecdysteroid-UDP-glucosyltransferase and cholesterol oxidase; ecdysone inhibitor; HMG-CoA reductase; ion channel inhibitors such as sodium channel inhibitor and calcium channel inhibitor; juvenile hormone esterase; diuretic hormone acceptors; stilbene synthetase; bibenzyl synthetase; chitinase; and glucanase.

The toxins expressed in these transgenic plants include hybrid toxins, partially deficient toxins and modified toxins, which derive from δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and insecticidal proteins such as VIP1, VIP2, VIP3 and VIP3A. The hybrid toxins are fabricated by a novel combination of the different domains of these proteins, using genetic recombination technology. The known partially deficient toxin is Cry1Ab, in which a part of amino acid sequence is deficient. In modified toxins, one or more amino acids of a natural toxin are replaced. Examples of these toxins and transgenic plants capable of synthesizing these toxins are described in EP-A-0 374 753, WO 93/07278, WO 95/34656, EP-A-0 427 529, EP-A-451 878, and WO 03/052073. The toxins contained in these transgenic plants impart resistance to insect pests of Coleoptera, insect pests of Diptera and insect pests of Lepidoptera to the plants.

There have already been known transgenic plants having one or more insecticidal pest-resistant genes and capable of producing one or more toxins, and some of them are commercially available. Examples of the transgenic plants include YieldGard (registered trademark) (a corn variety expressing Cry1Ab toxin), YieldGard Rootworm (registered trademark) (a corn variety expressing Cry3Bb1 toxin), YieldGard Plus (registered trademark) (a corn variety expressing Cry1Ab and Cry3Bb1 toxins), Herculex I (registered trademark) (a corn variety expressing Cry1Fa2 toxin and phosphinothricin N-acetyltransferase (PAT) to impart resistance to glufosinate), NatureGard (registered trademark), AGRISURE (registered trademark) CB Advantage (Bt11 cornborer (CB) character), and Protecta (registered trademark).

There have already been known transgenic cottons having one or more insecticidal pest-resistant genes and capable of producing one or more toxins, and some of them are commercially available. Examples of the transgenic cottons include BollGard (registered trademark) (cotton cultivar expressing a Cry1Ac toxin), BollGard (registered trademark) II (cotton cultivar expressing Cry1Ac and Cry2Ab toxins), BollGard (registered trademark) III (cotton cultivar expressing Cry1Ac, Cry2Ab and VIP3A toxins), VipCot (registered trademark) (cotton cultivar expressing a VIP3A and Cry1Ab toxins) and WideStrike (registered trademark) (cotton cultivar expressing Cry1Ac and Cry1F toxins).

Examples of the plant used in the present invention include plants imparted with resistance to aphidas, such as soybean having a Rag1 (ResistanceAphidGene1) gene introduced thereinto.

The above crops also include those imparted with a capacity of producing an anti-pathogenic substance having selective activity. As the anti-pathogenic substance, PR proteins (PRPs, EP-A-0 392 225) are known. These anti-pathogenic substances and transgenic plants producing thereof are described in EP-A-0 392 225, WO 95/33818, and EP-A-0 353 191. Examples of the anti-pathogenic substance expressed by the transgenic plants include ion channel inhibitors such as a sodium channel inhibitor and calcium channel inhibitor (KP1, KP4 and KP6 toxins produced by viruses are known); stilbene synthases; bibenzyl synthases; chitinase; glucanase; PR proteins; and substances produced by microorganisms, such as peptide antibiotics, antibiotics having a heterocyclic ring and protein factors (called genes resistant to plant diseases and are described in WO 03/000906) involved in plant disease resistance.

The above crops include those imparted with useful traits, such as reformed oil component and enhanced amino acid content, by means of a genetic recombination technique. The crops are exemplified by VISTIVE (registered trademark) (low linolenic soybean with reduced linolenic acid content) and high-lysine (high-oil) corn (corn with increased lysine or oil content).

The crops further include stacked varieties, which are fabricated by combining the above classical herbicidal traits or herbicide resistant genes, insecticidal pest resistant genes, anti-pathogenic substance-producing genes, reformed oil component and enhanced amino acid content.

The above-mentioned crops include those imparted with tolerance to diseases, tolerance to dehydration stresses, traits to increase sugar content, and so on.

The present invention composition can control weeds effectively in, especially, soybean fields, cotton fields, and corn fields.

Examples of weeds capable of controlling the composition of the present invention include the followings.

Urticaceae weeds: anual nettle (*Urtica urens*);

Polygonaceous weeds: wild buckwheat (*Polygonum convolvulus*), pale smartweed (*Polygonum lapathifolium*), pennsylvania smartweed (*Polygonum pensylvanicum*), ladysthumb (*Polygonum persicaria*), tufted knotweed (*Polygonum longisetum*), knotweed (*Polygonum aviculare*), common knotweed (*Polygonum arenastrum*), Japanese knotweed (*Polygonum cuspidatum*), Japanese dock (*Rumex japonicus*), curly dock (*Rumex crispus*), broad-leaved dock (*Rumex obtusifolius*), and Sorrel (*Rumex acetosa*);

Portulacaceous weeds: common purslane (*Portulaca oleracea*);

Caryophyllaceous weeds: common chickweed (*Stellaria media*), mouse ear chickweed (*Cerastium holosteoides*), sticky chickweed (*Cerastium glomeratum*), corn spurry (*Spergula arvensis*), and common catchfly (*Silene gallica*);

Molluginaceae weeds: carpetweed (*Mollugo verticillata*)

Chenopodiaceous weeds: common lambsquarters (*Chenopodium album*), American wormseed (*Chenopodium ambrosioides*), burningbush (*Kochia scoparia*), tumble weed (*Salsola kali*), and *Atriplex* spp.;

Amaranthaceous weeds: redroot pigweed (*Amaranthus retroflexus*), slender amaranth (*Amaranthus viridis*), livid amaranth (*Amaranthus lividus*), spiny amaranth (*Amaranthus spinosus*), smooth pigweed (*Amaranthus hybridus*), palmer amaranth (*Amaranthus palmeri*), common waterhemp (*Amaranthus rudis*), smooth pigweed (*Amaranthus patulus*), rough-fruit amaranth (*Amaranthus tuberculatos*), mat amaranth (*Amaranthus blitoides*), large-fruited amaranth (*Amaranthus deflexus*), *Amaranthus quitensis*, alligatorweed (*Alternanthera philoxeroides*), alligator weed (*Alternanthera sessilis*), and Sanguinarea (*Alternanthera tenella*);

Papaveraceae weeds: corn poppy (*Papaver rhoeas*) and Mexican prickly poppy (*Argemone mexicana*);

Cruciferous weeds: wild radish (*Raphanus raphanistrum*), radish (*Raphanus sativus*), wild mustard (*Sinapis arvensis*), shepherd spurse (*Capsella bursa-pastoris*), brown mustard (*Brassica juncea*), wild turnip (*Brassica campestris*), tansy mustard (*Descurainia pinnata*), yellow marsh-cress (*Rorippa islandica*), yellow fieldcress (*Rorippa sylvestris*), field penny-cress (*Thlaspi arvense*), annual bastard-cabbage (*Myagrum rugosum*), Virginia pepperweed (*Lepidium virginicum*), and lesser swinecress (*Coronopus didymus*);

Capparaceae weeds: *Cleome affinis;*

Leguminosae weeds: indian jointvetch (*Aeschynomene indica*), zigzag jointvetch (*Aeschynomene rudis*), coffeeweed (*Sesbania exaltata*), sicklepod (*Cassia obtusifolia*), coffee senna (*Cassia occidentalis*), dixie ticktrefoil (*Desmodium tortuosum*), bush groundnut (*Desmodium adscendens*), Dutch clover (*Trifolium repens*), kudzu (*Pueraria lobata*), common vetch (*Vicia angustifolia*), hairy indigo (*Indigofera hirsuta*), *Indigofera truxillensis*, and cowpea (*Vigna sinensis*);

Oxalidaceous weeds: woodsorrel (*Oxalis corniculata*), yellow wood sorrel (*Oxalis strica*), and *Oxalis oxyptera;*

Geraniaceae weeds: carolina geranium (*Geranium carolinense*) and redstem storksbill (*Erodium cicutarium*);

Euphorbiaceous weeds: sun spurge (*Euphorbia helioscopia*), spotted spurge (*Euphorbia maculata*), prostrate spurge (*Euphorbia humistrata*), leafy spurge (*Euphorbia esula*), Mexican fireplant (*Euphorbia heterophylla*), para rubber tree (*Euphorbia brasiliensis*), Australian acalypha (*Acalypha australis*), tropic croton (*Croton glandulosus*), lobed croton (*Croton lobatus*), Mascarene island leaf-flower (*Phyllanthus corcovadensis*), and castor bean (*Ricinus communis*);

Malvaceous weeds: velvetleaf (*Abutilon theophrasti*), arrowleaf sida (*Sida rhombifora*), flannelweed (*Sida cordifolia*), prickly sida (*Sida spinosa*), *Sida glaziovii*, *Sida santaremnensis*, venice mallow (*Hibiscus trionum*), spurred anoda (*Anoda cristata*), and broomweed (*Malvastrum coromandelianum*);

Sterculioideae weeds: uhaloa (*Waltheria indica*);

Violaceous weeds: field pansy (*Viola arvensis*) and wild pansy (*Viola tricolor*);

Cucurbitaceae weeds: burcucumber (*Sicyos angulatus*), wild cucumber (*Echinocystis lobata*), and bitter cucumber (*Momordica charantia*);

Lythraceae weeds: purple loosestrife (*Lythrum salicaria*);

Apiaceae weeds: water pennywort (*Hydrocotyle sibthorpioides*);

Sapindaceae weeds: balloon vine (*Cardiospermum halicacabum*);

Primulaceae weeds: Scarlet pimpernel (*Anagallis arvensis*);

Asclepiadaceae weeds: common milkweed (*Asclepias syriaca*) and honeyvine milkweed (*Ampelamus albidus*);

Rubiaceous weeds: catchweed bedstraw (*Galium aparine*), catchweed (*Galium spurium* var. *echinospermon*), broadleaf buttonweed (*Spermacoce latifolia*), Mexican clover (*Richardia brasiliensis*), and winged false buttonweed (*Borreria alata*);

Convolvulaceous weeds: Japanese morning glory (*Ipomoea nil*), ivyleaf morning glory (*Ipomoea hederacea*), tall morning glory (*Ipomoea purpurea*), entireleaf morning glory (*Ipomoea hederacea* var. *integriuscula*), pitted morning glory (*Ipomoea lacunosa*), threelobe morning glory (*Ipomoea triloba*), blue morning glory (*Ipomoea acuminata*), scarlet morning glory (*Ipomoea hederifolia*), red morning glory (*Ipomoea coccinea*), cypressvine morning glory (*Ipomoea quamoclit*), *Ipomoea grandifolia*, *Ipomoea aristolochiafolia*, ivy-leaved morning glory (*Ipomoea cairica*), field bindweed (*Convolvulus arvensis*), Japanese false bindweed (*Calystegia hederacea*), Japanese bindweed (*Calystegia japonica*), german ivy (*Merremia hedeacea*), hairy woodrose (*Merremia aegyptia*), roadside woodrose (*Merremia cissoides*), and hairy clustervine (*Jacquemontia tamnifolia*);

Boraginaceous weeds: forget-me-not (*Myosotis arvensis*);

Labiate weeds: purple deadnettle (*Lamium purpureum*), henbit deadnettle (*Lamium amplexicaule*), christmas candlestick (*Leonotis nepetaefolia*), pignut (*Hyptis suaveolens*), *Hyptis lophanta*, honeyweed (*Leonurus sibiricus*), and stagger weed (*Stachys arvensis*);

Solanaceous weeds: jimsonweed (*Datura stramonium*), black nightshade (*Solanum nigrum*), American nightshade (*Solanum americanum*), Eastern black nightshade (*Solanum ptycanthum*), hairy nightshade (*Solanum sarrachoides*), buffalobur (*Solanum rostratum*), Dutch eggplant (*Solanum aculeatissimum*), sticky nightshade (*Solanum sisymbriifolium*), horsenettle (*Solanum carolinense*), ground cherry (*Physalis angulata*), smooth groundcherry (*Physalis subglabrata*), and shoo-fly plant (*Nicandra physaloides*);

Scrophulariaceae weeds: ivyleaf speedwell (*Veronica hederaefolia*), Persian speedwell (*Veronica persica*), and corn speedwell *Veronica arvensis*);

Plantaginaceae weed: Chinese plantain (*Plantago asiatica*);

Compositae weeds: common cocklebur (*Xanthium pensylvanicum*), noogoora burr (*Xanthium occidentale*), common sunflower (*Helianthus annuus*), chamomile (*Matricaria cha-*

*momilla*), scentess chamomile (*Matricaria perforata*), corn marigold (*Chrysanthemum segetum*), pineappleweed (*Matricaria matricarioides*), mugwort (*Artemisia princeps*), common mugwort (*Artemisia vulgaris*), Chinese mugwort (*Artemisia verlotorum*), tall goldenrod (*Solidago altissima*), dandelion (*Taraxacum officinale*), hairy galinsoga (*Galinsoga ciliata*), Smallfower galinsoga (*Galinsoga parviflora*), common groundsel (*Senecio vulgaris*), *Senecio brasiliensis, Senecio grisebachii*, hairy fleabane (*Conyza bonariensis*), Horseweed (*Conyza canadensis*), ragweed (*Ambrosia artemisiaefolia*), giant ragweed (*Ambrosia trifida*), Hairy beggerticks (*Bidens pilosa*), devil's beggartick (*Bidens frondosa*), *Bidens subalternans*, creeping thistle (*Cirsium arvense*), bull thistle (*Cirsium vulgare*), milk thistle (*Silybum marianum*), musk thistle (*Carduus nutans*), prickly lettuce (*Lactuca serriola*), sow thistle (*Sonchus oleraceus*), spiny sowthistle (*Sonchus asper*), beach creeping oxeye (*Wedelia glauca*), perfoliate blackfoot (*Melampodium perfoliatum*), cupid's shaving brush (*Emilia sonchifolia*), wild marigold (*Tagetes minuta*), para cress (*Blainvillea latifolia*), coat buttons (*Tridax procumbens*), yerba porosa (*Porophyllum ruderale*), paraguay starbur (*Acanthospermum australe*), bristly starbur (*Acanthospermum hispidum*), heart seed (*Cardiospermum halicacabum*), blue top (*Ageratum conyzoides*), common boneset (*Eupatorium perfoliatum*), false daisy (*Eclipta alba*), American burnweed (*Erechtites hieracifolia*), American everlasting (*Gamochaeta spicata*), shiny cudweed (*Gnaphalium spicatum*), *Jaegeria hirta*, carrot grass (*Parthenium hysterophorus*), Menamomi (*Siegesbeckia orientalis*), and weeping lovegrass (*Soliva sessilis*);

Liliaceae weeds: wild onion (*Allium canadense*) and wild garlic (*Allium vineale*);

Commelinaceae weeds: asiatic dayflower (*Commelina communis*), Bengal dayflower (*Commelina bengharensis*), and erect dayflower (*Commelina erecta*);

Graminaceous weeds: barnyardgrass (*Echinochloa crusgalli*), green foxtail (*Setaria viridis*), giant foxtail (*Setaria faberi*), yellow foxtail (*Setaria glauca*), knotroot foxtail (*Setaria geniculata*), southern crabgrass (*Digitaria ciliaris*), large crabgrass (*Digitaria sanguinalis*), Jamaican crabgrass (*Digitaria horizontalis*), sourgrass (*Digitaria insularis*), goosegrass (*Eleusine indica*), annual bluegrass (*Poa annua*), orange foxtail (*Alospecurus aequalis*), blackgrass (*Alopecurus myosuroides*), wild oat (*Avena fatua*), johnsongrass (*Sorghum halepense*), shattercane (*Sorghum vulgare*), quackgrass (*Agropyron repens*), Italian ryegras (*Lolium multiflorum*), perennial ryegrass (*Lolium perenne*), wimmera ryegrass (*Lolium rigidum*), rye brome (*Bromus secalinus*), downy brome (*Bromus tectorum*), foxtail barley (*Hordeum jubatum*), goatgrasses (*Aegilops cylindrica*), reed canarygrass (*Phalaris arundinacea*), lesser cabrygrass (*Phalaris minor*), silky bentgrass (*Apera spica-venti*), fall panicum (*Panicum dichotomiflorum*), Texas panicum (*Panicum texanum*), Guinea grass (*Panicum maximum*), broadleaf signaigrass (*Brachiaria platyphylla*), ruzigrass (*Brachiaria ruziziensis*), alexandergrass (*Brachiaria plantaginea*), surinam grass (*Brachiaria decumbens*), pallisade grass (*Brachiaria brizantha*), koronivia grass (*Brachiaria humidicola*), common sandbur (*Cenchrus echinatus*), spiny burr grass (*Cenchrus pauciflorus*), woolly cupgrass (*Eriochloa villosa*), Pennisetum (*Pennisetum setosum*), rhodes grass (*Chloris gayana*), Jersey love grass (*Eragrostis pilosa*), ruby grass (*Rhynchelitrum repens*), crowfoot grass (*Dactyloctenium aegyptium*), ribbed murainagrass (*Ischaemum rugosum*), rice (*Oryza sativa*), bahia grass (*Paspalum notatum*), coastal sand *paspalum* (*Paspalum maritimum*), kikuyugrass (*Pennisetum clandestinum*), fountaingrass (*Pennisetum setosum*), and itch grass (*Rottboellia cochinchinensis*);

Cllitrichaceae weeds: amur *cyperus* (*Cyperus microiria*), ricefield flatsedge (*Cyperus iria*), rice flatsedge (*Cyperus odoratus*), nut grass (*Cyperus rotundus*), yellow nutsedge (*Cyperus esculentus*), and pasture spikesedge (*Kyllinga gracillima*); and Equisetaceous weeds: field horsetail (*Equisetum arvense*) and marsh horsetail (*Equisetum palustre*).

In the present invention composition, the mixing ratio, expressed in weight ratio, of the one or more compounds selected from Group A to isoxaflutole is within the range of from 1:0.01 to 1:100, preferably from 1:0.05 to 1:50, more preferably from 1:0.1 to 1:10.

In the present invention composition, the mixing ratio, expressed in weight ratio, of the one or more compounds selected from Group A to cyprosulfamide is within the range of from 1:0.01 to 1:100, preferably from 1:0.05 to 1:50, more preferably from 1:0.1 to 1:10.

In the present invention composition, the mixing ratio, expressed in weight ratio, of the one or more compounds selected from Group A:isoxaflutole:cyprosulfamide is within the range of 1:0.01-100:0.01-100, preferably 1:0.05-50:0.05-50, more preferably 1:0.1-10:0.1-10.

Usually, the present invention composition is formulated to emulsifiable concentrates, wettable powders, suspensible concentrates, granules, and so on by being mixed with a solid carrier, a liquid carrier, or the like, and optionally with surfactants and other auxiliaries for formulation. These formulations generally contain 0.1 to 90% by weight, preferably about 1 to about 80% by weight of the total amount of isoxaflutole, cyprosulfamide, and the one or more compounds selected from Group A.

Examples of the solid carrier used for formulating the composition of the present invention include fine powders and granules of clays such as kaolinite, diatomaceous earth, synthetic hydrated silica, Fubasami clay, bentonite and acid clay; talc; other inorganic minerals such as sericite, quartz powder, sulfur powder, activated carbon and calcium carbonate; and chemical fertilizer such as ammonium sulfate, ammonium phosphate, ammonium nitrate, ammonium chloride and urea. Examples of the liquid carrier include water; alcohols such as methanol and ethanol; ketones such as acetone, methyl ethyl ketone and cyclohexanone; aromatic hydrocarbons such as toluene, xylene, ethylbenzene and methylnaphthalene; non-aromatic hydrocarbons such as hexane, cyclohexane and kerosene; esters such as ethyl acetate and butyl acetate; nitriles such as acetonitrile and isobutyronitrile; ethers such as dioxane and diisopropyl ether; acid amides such as dimethylformamide and dimethylacetamide; and halogenated hydrocarbons such as dichloroethane and trichloroethylene.

Examples of the surfactant used for formulating the composition of the present invention include alkyl sulfate esters, alkylsulfonate salts, alkylarylsulfonate salts, alkylaryl ethers, polyoxyethylene alkylaryl ethers, polyethylene glycol ethers, polyhydric alcohol esters and sugar alcohol derivatives. Examples of the other auxiliary for formulation include sticking agents and dispersants, such as casein; gelatin; polysaccharides such as starch, gum arabic, cellulose derivatives and alginic acid; lignin derivatives; bentonite; and synthetic water-soluble polymers such as polyvinyl alcohol, polyvinylpyrrolidone and polyacrylic acid; and stabilizers such as PAP (isopropyl acid phosphate), BHT (2,6-tert-butyl-4-methylphenol), BHA (2-/3-tert-butyl-4-methoxyphenol), vegetable oil, mineral oil, fatty acid and fatty acid ester.

The present invention composition can also be prepared by formulating each of the active ingredients by the above-described procedure, and then mixing the resulting formulations.

The present invention composition formulated can be applied as it is to a soil or a plant or alternatively may be applied to a soil or a plant after being diluted with water or the like. Moreover, the present invention composition may be used for increasing herbicidal activities by being used in admixture with another herbicide. Furthermore, the present invention composition can be used together with insecticides, fungicides, plant growth regulators, fertilizers, soil-improving agents, and so on.

Examples of herbicides with which the composition of the present invention may be mixed include the following.

2,4-D, 2,4-D-ammonium, 2,4-D-butotyl, 2,4-D-2-butoxypropyl, 2,4-D-3-butoxypropyl, 2,4-D-butyl, 2,4-D-diethylammonium, 2,4-D-dimethylammonium, 2,4-D-diolamine, 2,4-D-dodecylammonium, 2,4-D-ethyl, 2,4-D-2-ethylhexyl, 2,4-D-heptylammonium, 2,4-D-isooctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2,4-D-choline, 2,4-DB, 2,4-DB-dimethylammonium, 2,4-DB-isooctyl, 2,4-DB-butyl, 2,4-DB-sodium, 2,4-DB-potassium, 2,4-DB-choline, MCPA, MCPA-dimethylammonium, MCPA-2-ethylhexyl, MCPA-isooctyl, MCPA-butotyl, MCPA-butyl, MCPA-diolamine, MCPA-ethyl, MCPA-isobutyl, MCPA-isopropyl, MCPA-methyl, MCPA-olamine, MCPA-sodium, MCPA-trolamine, MCPA-choline, MCPB, MCPB-ethyl, MCPB-methyl, MCPB-sodium, MCPB-choline, mecoprop, mecoprop-dimethylammonium, mecoprop-diolamine, mecoprop-ethadyl, mecoprop-2-ethylhexyl, mecoprop-isooctyl, mecoprop-methyl, mecoprop-potassium, mecoprop-sodium, mecoprop-trolamine, mecoprop-choline, mecoprop-P, mecoprop-P-dimethylammonium, mecoprop-P-2-ethylhexyl, mecoprop-P-isobutyl, mecoprop-P-potassium, mecoprop-P-choline, dichlorprop, dichlorprop-butotyl, dichlorprop-dimethylammonium, dichlorprop-ethylammonium, dichlorprop-2-ethylhexyl, dichlorprop-isooctyl, dichlorprop-methyl, dichlorprop-potassium, dichlorprop-sodium, dichlorprop-choline, dichlorprop-P, dichlorprop-P-dimethylammonium, dichlorprop-P-2-ethylhexyl, dichlorprop-choline, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicamba-choline, bromoxynil, bromoxynil-octanoate, dichlobenil, ioxynil, ioxynil-octanoate, di-allate, butylate, tri-allate, phenmedipham, chlorpropham, asulam, phenisopham, benthiocarb, molinate, esprocarb, pyributicarb, prosulfocarb, orbencarb, EPTC, dimepiperate, swep, propachlor, metazachlor, alachlor, acetochlor, metolachlor, S-metolachlor, butachlor, pretilachlor, thenylchlor, aminocyclopyrachlor, aminocyclopyrachlor-methyl, aminocyclopyrachlor-potassium, trifluralin, pendimethalin, ethalfluralin, benfluralin, prodiamine, simazine, atrazine, propazine, cyanazine, ametryn, simetryn, dimethametryn, prometryn, indaziflam, triaziflam, metribuzin, hexazinone, isoxaben, diflufenican, diuron, linuron, fluometuron, difenoxuron, methyldymron, isoproturon, isouron, tebuthiuron, benzthiazuron, methabenzthiazuron, propanil, mefenacet, clomeprop, naproanilide, bromobutide, daimuron, cumyluron, etobenzanid, bentazon, tridiphane, indanofan, amitrole, fenchlorazole, clomazone, maleic hydrazide, pyridate, chloridazon, norflurazon, bromacil, terbacil, oxaziclomefone, cinmethylin, benfuresate, cafenstrole, carfentrazone-ethyl, flumiclorac-pentyl, pyrithiobac, pyrithiobac-sodium, pyriminobac, pyriminobac-methyl, bispyribac, bispyribac-sodium, pyribenzoxim, pyrimisulfan, pyriftalid, triafamone, fentrazamide, dimethenamid, dimethenamid-P, ACN, benzobicyclon, dithiopyr, triclopyr, triclopyr-butotyl, triclopyr-ethyl, triclopyr-triethylammonium, thiazopyr, fluoroxypyr, fluoroxypyr-meptyl, aminopyralid, aminopyralid-potassium, aminopyralid-tris(2-hydroxypropyl)ammonium), aminopyralid-choline, clopyralid, clopyralid-methyl, clopyralid-olamine, clopyralid-potassium, clopyralid-tris(2-hydroxypropyl)ammonium, clopyralid-choline, dalapon, chlorthiamid, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron, chlorsulfuron, cinosulfuron, ethametsulfuron, ethametsulfuron-methyl, iodosulfuron, iodosulfuron-methyl-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, picolinafen, beflubutamid, mesotrione, sulcotrione, tefuryltrione, tembotrione, isoxachlortole, benzofenap, pyrasulfotole, pyrazolynate, pyrazoxyfen, topramezone, flupoxam, amicarbazone, bencarbazone, flucarbazone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium, imazapic, imazapic-ammonium, imazapyr, imazaquin, imazethapyr, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, pyroxasulfone, glyphosate, glyphosate-isopropylamine, glyphosate-trimethylsulfonium, glyphosate-ammonium, glyphosate-diammonium, glyphosate-sodium, glyphosate-potassium, glyphosate guanidine derivative salts, glufosinate, glufosinate-ammonium, glufosinate-P, glufosinate-P-sodium, glufosinate-P-ammonium, bialafos, anilofos, bensulide, butamifos, paraquat, paraquat-dichloride, diquat and diquat-dibromide.

While the dosage of the present invention composition depends upon the mixing ratio of isoxaflutole, cyprosulfamide, and the one or more compounds selected from Group A, weather conditions, formulation types, application time, application methods, application places, objective weeds, and objective crops, and it is usually 1 to 3000 g per hectare, which is expressed in the amount of active ingredients of isoxaflutole, cyprosulfamide, and the one or more compounds selected from Group A in total. An emulsifiable concentrate, a wettable powder, a suspensible concentrate, and so on are applied usually with dilution with 100 to 2000 liters of water per hectare such that the above-described amount of active ingredients may be achieved. Further, when the present invention composition is applied to weeds by foliar treatment, it is expected to enhance a herbicidal effect against weeds by adding an adjuvant to the diluted liquid of the present invention composition.

The present invention composition is applied to weeds or a place where weeds are to emerge. The application to weeds may be application to weeds per se or application to a soil where weeds have emerged. The application to a place where weeds are to emerge may be application to the surface of a soil where weeds have not emerged yet.

Examples of the application method of the present invention composition include the following embodiments:
a method of spreading the composition over the surface of a soil before sowing seeds of crops and before weed emergence;
a method of spreading the composition over the surface of a soil before sowing seeds of crops and after weed emergence;
a method of spraying the composition over weeds before sowing seeds of crops and after weed emergence;
a method of spreading the composition over a surface of the soil after sowing seeds of crops, before emergence of the crops, and before weed emergence;
a method of spreading the composition over the surface of a soil after sowing seeds of crops, before emergence of the crops, and after weed emergence;
a method of spreading the composition over weeds after sowing seeds of crops, before emergence of the crops, and after weed emergence;
a method of spreading the composition over the surface of a soil in the presence of crops, before weed emergence;
a method of spreading the composition over the surface of a soil in the presence of crops, after weed emergence; and/or
a method of spreading the composition over weeds in the presence of crops, after weed emergence.

EXAMPLES

The present invention will be described in more detail below by the following Examples, but the present invention is not limited to the Examples.
[Formulation]
Formulation Examples are described below. In the following Examples, all the "parts" are by weight unless otherwise stated.

Formulation Example 1

A wettable formulation is obtained by thoroughly pulverizing and mixing 2 parts of flumioxazin, 20 parts of isoxaflutole, 20 parts of cyprosulfamide, 2 parts of sodium lauryl sulfate, and 56 parts of synthetic hydrous silicon oxide.

Formulation Example 2

A wettable formulation is obtained by thoroughly pulverizing and mixing 20 parts of flumioxazin, 2 parts of isoxaflutole, 2 parts of cyprosulfamide, 2 parts of sodium lauryl sulfate, and 74 parts of synthetic hydrous silicon oxide.

Formulation Example 3

A wettable formulation is obtained by thoroughly pulverizing and mixing 2 parts of saflufenacil, 20 parts of isoxaflutole, 20 parts of cyprosulfamide, 2 parts of sodium lauryl sulfate, and 56 parts of synthetic hydrous silicon oxide.

Formulation Example 4

A wettable formulation is obtained by thoroughly pulverizing and mixing 20 parts of saflufenacil, 2 parts of isoxaflutole, 2 parts of cyprosulfamide, 2 parts of sodium lauryl sulfate, and 74 parts of synthetic hydrous silicon oxide.

Formulation Example 5

A suspension formulation is obtained by mixing 2 parts of sulfentrazone, 20 parts of isoxaflutole, 20 parts of cyprosulfamide, 3 parts of polyoxyethylene sorbitan monooleate, 3 parts of CMC (carboxymethylcellulose), and 52 parts of water, and wet-pulverizing the mixture until the particle size becomes 5 µm or smaller.

Formulation Example 6

An emulsifiable concentrate is obtained by mixing 2 parts of fomesafen-sodium, 2 parts of isoxaflutole, 2 parts of cyprosulfamide, 14 parts of polyoxyethylene stearyl phenyl ether, 6 parts of calcium dodecylbenzene sulfonate, 30 parts of xylene, and 44 parts of N,N-dimethylformamide.

Formulation Example 7

An emulsifiable concentrate is obtained by mixing 2 parts of oxyfluorfen, 2 parts of isoxaflutole, 2 parts of cyprosulfamide, 14 parts of polyoxyethylene stearylphenyl ether, 6 parts of calcium dodecylbenzene sulfonate, 30 parts of xylene, and 44 parts of N,N-dimethylformamide.

Formulation Example 8

An emulsifiable concentrate is obtained by mixing 2 parts of Compound 1, 2 parts of isoxaflutole, 2 parts of cyprosulfamide, 14 parts of polyoxyethylene stearyl phenyl ether, 6 parts of calcium dodecylbenzene sulfonate, 30 parts of xylene, and 44 parts of N,N-dimethylformamide.
[Herbicidal Activity]

The herbicidal activity is evaluated by dividing the activity into 0 to 100, wherein "0" indicates that the emergence or growing state of a test weed at the examination has no or little difference from that of an untreated control, and "100" indicates that a test plant is completely withered and died, or their emergence or growth is completely inhibited.

Example 1

*Amaranthus retroflexus* and *Digitaria ciliaris* were sowed on a plastic pot filled with a soil. Following the sowing, on the day of the sowing, a mixed liquid of flumioxazin, isoxaflutole, and cyprosulfamide was sprayed uniformly so that the amounts of the agents might become those shown in Tables 1 in a sprayed water amount of 500 L/ha. The mixed liquid of flumioxazin, isoxaflutole, and cyprosulfamide was prepared by dissolving the respective compounds in prescribed amounts separately in acetone containing 2% (w/v) of Tween 20 (surfactant, produced by Tokyo Chemical Industry Co., Ltd.), diluting the respective solutions with water and then combining them, followed by dilution with water so that the final acetone concentration of the spray liquid might be 10% by volume. After the spray treatment, the pot was carried into a greenhouse. Thirty one days after the spray treatment, seeds of corn (species: Pioneer 31P41), seeds of soybean (species: Williams 82), and seeds of cotton (species: unknown) were sowed. Thirty days after the spray treatment, the herbicidal activity was evaluated.

The results are shown in Table 1.

TABLE 1

| Test compounds | Amounts of ingredients (g/ha) | Herbicidal activity | |
|---|---|---|---|
| | | *Amaranthus retroflexus* | *Digitaria ciliaris* |
| Flumioxazin | 2 | 100 | 100 |
| + Isoxaflutole | + 20 | | |
| + Cyprosulfamide | + 20 | | |
| | 20 | 100 | 100 |
| | + 2 | | |
| | + 2 | | |

Example 2

*Ipomoea hederacea* was sowed on a plastic pot filled with a soil. Following the sowing, on the day of the sowing, a mixed liquid of flumioxazin, isoxaflutole, and cyprosulfamide was sprayed uniformly so that the amounts of the agents might become those shown in Table 2 in a sprayed water amount of 500 L/ha. The mixed liquid of flumioxazin, isoxaflutole, and cyprosulfamide was prepared by dissolving the respective compounds in prescribed amounts separately in acetone containing 2% (w/v) of Tween 20 (surfactant, produced by Tokyo Chemical Industry Co., Ltd.), diluting the respective solutions with water and then combining them, followed by dilution with water so that the final acetone concentration of the spray liquid might be 10% by volume. After the spray treatment, the pot was carried into a greenhouse. Ten days after the spray treatment, the herbicidal activity to *Ipomoea hederacea* was evaluated.

The results are shown in Table 2.

TABLE 2

| Test compounds | Amounts of ingredients (g/ha) | Herbicidal activity *Ipomoea hederacea* |
|---|---|---|
| Flumioxazin | 20 | 100 |
| + Isoxaflutole | + 2 | |
| + Cyprosulfamide | + 2 | |
| Flumioxazin | 20 | 80 |
| Isoxaflutole | 2 | 0 |
| + Cyprosulfamide | + 2 | |

Example 3

*Echinochloa crus-galli* was sowed on a plastic pot filled with a soil. Following the sowing, on the day of the sowing, a mixed liquid of flumioxazin, isoxaflutole, and cyprosulfamide was sprayed uniformly so that the amounts of the agents might become those shown in Table 3 in a sprayed water amount of 500 L/ha. The mixed liquid of flumioxazin, isoxaflutole, and cyprosulfamide was prepared by dissolving the respective compounds in prescribed amounts separately in acetone containing 2% (w/v) of Tween 20 (surfactant, produced by Tokyo Chemical Industry Co., Ltd.), diluting the respective solutions with water and then combining them, followed by dilution with water so that the final acetone concentration of the spray liquid might be 10% by volume.

After the spray treatment, the pot was carried into a greenhouse. Twenty days after the spray treatment, the herbicidal activity to *Echinochloa crus-galli* was evaluated.

The results are shown in Table 3.

TABLE 3

| Test compounds | Amounts of ingredients (g/ha) | Herbicidal activity *Echinochloa crus-galli* |
|---|---|---|
| Flumioxazin | 2 | 90 |
| + Isoxaflutole | + 20 | |
| + Cyprosulfamide | + 20 | |
| Flumioxazin | 2 | 10 |
| Isoxaflutole | 20 | 60 |
| +Cyprosulfamide | + 20 | |

Example 4

*Amaranthus retroflexus, Ipomoea hederacea, Echinochloa crus-galli,* and *Digitaria ciliaris* are sowed on a plastic pot filled with a soil. Following the sowing, on the day of the sowing, a mixed liquid of sulfentrazone, isoxaflutole, and cyprosulfamide is sprayed uniformly. After the spray treatment, the pot is carried into a greenhouse. As a result, an excellent herbicidal activity is observed.

Example 5

*Amaranthus retroflexus, Ipomoea hederacea, Echinochloa crus-galli,* and *Digitaria ciliaris* are sowed on a plastic pot filled with a soil. Following the sowing, on the day of the sowing, a mixed liquid of saflufenacil, isoxaflutole, and cyprosulfamide is sprayed uniformly. After the spray treatment, the pot is carried into a greenhouse. As a result, an excellent herbicidal activity is observed.

Example 6

*Amaranthus retroflexus, Ipomoea hederacea, Echinochloa crus-galli,* and *Digitaria ciliaris* are sowed on a plastic pot filled with a soil. Following the sowing, on the day of the sowing, a mixed liquid of oxyfluorfen, isoxaflutole, and cyprosulfamide is sprayed uniformly. After the spray treatment, the pot is carried into a greenhouse. As a result, an excellent herbicidal activity is observed.

Example 7

*Amaranthus retroflexus, Ipomoea hederacea, Echinochloa crus-galli,* and *Digitaria ciliaris* are sowed on a plastic pot filled with a soil. Following the sowing, on the day of the sowing, a mixed liquid of fomesafen-sodium, isoxaflutole, and cyprosulfamide is sprayed uniformly. After the spray treatment, the pot is carried into a greenhouse. As a result, an excellent herbicidal activity is observed.

Example 8

*Amaranthus retroflexus, Ipomoea hederacea, Echinochloa crus-galli,* and *Digitaria ciliaris* are sowed on a plastic pot filled with a soil. Following the sowing, on the day of the sowing, a mixed liquid of Compound 1, isoxaflutole, and cyprosulfamide is sprayed uniformly. After the spray treatment, the pot is carried into a greenhouse. As a result, an excellent herbicidal activity is observed.

Example 9

To the surface of a soil in a pot where grape, Satsuma mandarin, peach, and almond are cultivated is sprayed uniformly a mixed liquid of flumioxazin, isoxaflutole, and cyprosulfamide.

The plants are grown outdoors. As a result, a high herbicidal activity to weeds is observed.

Example 10

To the surface of a soil in a pot where grape, Satsuma mandarin, peach, and almond are cultivated is sprayed uniformly a mixed liquid of sulfentrazone, isoxaflutole, and cyprosulfamide.

The plants are grown outdoors. As a result, a high herbicidal activity to weeds is observed.

Example 11

To the surface of a soil in a pot where grape, Satsuma mandarin, peach, and almond are cultivated is sprayed uniformly a mixed liquid of saflufenacil, isoxaflutole, and cyprosulfamide.

The plants are grown outdoors. As a result, a high herbicidal activity to weeds is observed.

Example 12

To the surface of a soil in a pot where grape, Satsuma mandarin, peach, and almond are cultivated is sprayed uniformly a mixed liquid of oxyfluorfen, isoxaflutole, and cyprosulfamide.

The plants are grown outdoors. As a result, a high herbicidal activity to weeds is observed.

Example 13

To the surface of a soil in a pot where grape, Satsuma mandarin, peach, and almond are cultivated is sprayed uniformly a mixed liquid of fomesafen-sodium, isoxaflutole, and cyprosulfamide.

The plants are grown outdoors. As a result, a high herbicidal activity to weeds is observed.

Example 14

To the surface of a soil in a pot where grape, Satsuma mandarin, peach, and almond are cultivated is sprayed uniformly a mixed liquid of Compound 1, isoxaflutole, and cyprosulfamide.

The plants are grown outdoors. As a result, a high herbicidal activity to weeds is observed.

The present invention makes it possible to control weeds in crop fields, vegetable fields, tree lands, or non-cultivated lands.

What is claimed is:

1. A herbicidal composition comprising as active ingredients isoxaflutole, cyprosulfamide and flumioxazin.

2. The herbicidal composition according to claim 1, wherein the weight ratio of flumioxazin to isoxaflutole is from 1:0.01 to 1:100.

3. The herbicidal composition according to claim 1, wherein the weight ratio of flumioxazin to cyprosulfamide is from 1:0.01 to 1:100.

4. A weed control method comprising applying isoxaflutole, cyprosulfamide and flumioxazin simultaneously or in combination to a soil of a place where weeds grow or are to grow, or to weeds.

5. The method according to claim 4, wherein the weight ratio of flumioxazin to isoxaflutole is within the range of from 1:0.01 to 1:100.

6. The method according to claim 4, wherein the weight ratio of flumioxazin to cyprosulfamide is within the range of from 1:0.01 to 1:100.

7. The method according to claim 4, wherein the place where weeds grow or are to grow is a soybean field, a cotton field, or a corn field.

8. The weed control method according to claim 7, wherein the soybean of the soybean field, the cotton of the cotton field, or the corn of the corn field is transgenic soybean, transgenic cotton, or transgenic corn.

9. The weed control method according to claim 7, wherein the soybean of the soybean field, the cotton of the cotton field, or the corn of the corn field is transgenic soybean, transgenic cotton, or transgenic corn to each of which resistance to herbicides has been imparted.

10. The weed control method according to claim 7, wherein the soybean of the soybean field or the cotton of the cotton field is transgenic soybean imparted with resistance to 4-hydroxyphenylpyruvate dioxygenase inhibitors or transgenic cotton imparted with resistance to 4-hydroxyphenylpyruvate dioxygenase inhibitors.

11. The method according to claim 4, wherein the place where weeds grow or are to grow is an orchard.

* * * * *